(12) United States Patent
Koslo et al.

(10) Patent No.: US 10,994,037 B1
(45) Date of Patent: May 4, 2021

(54) UVC SANITIZING ACCESSORY

(71) Applicant: SUPERIOR VENTURES LLC, Cleveland, OH (US)

(72) Inventors: Jonathan Koslo, Aurora, OH (US); Daniel DiCioccio, Painesville, OH (US); Justin Miller, Cleveland, OH (US)

(73) Assignee: Superior Ventures LLC, Cleveland, OH (US)

( * ) Notice: Subject to any disclaimer, the term of this patent is extended or adjusted under 35 U.S.C. 154(b) by 0 days.

(21) Appl. No.: 16/995,950

(22) Filed: Aug. 18, 2020

(51) Int. Cl.
| | |
|---|---|
| *A61L 2/10* | (2006.01) |
| *H04M 1/21* | (2006.01) |
| *H04M 1/17* | (2006.01) |
| *A61L 2/24* | (2006.01) |
| *A61L 2/26* | (2006.01) |

(52) U.S. Cl.
CPC ............ *A61L 2/10* (2013.01); *A61L 2/24* (2013.01); *A61L 2/26* (2013.01); *H04M 1/17* (2013.01); *H04M 1/21* (2013.01); *A61L 2202/00* (2013.01); *A61L 2202/14* (2013.01)

(58) Field of Classification Search
USPC .......................................................... 422/24
See application file for complete search history.

(56) References Cited

U.S. PATENT DOCUMENTS

| | | | | |
|---|---|---|---|---|
| 8,481,970 | B2* | 7/2013 | Cooper | A61L 2/10 |
| | | | | 250/455.11 |
| 8,668,727 | B2* | 3/2014 | Natale | A61N 5/062 |
| | | | | 607/88 |
| 9,550,004 | B2* | 1/2017 | Smetona | A61L 2/10 |
| 9,907,869 | B2* | 3/2018 | Bilenko | A61L 2/10 |
| 10,151,433 | B2* | 12/2018 | McLennan | F21L 4/045 |
| 2018/0280554 | A1* | 10/2018 | Khajavi | A61L 2/24 |

* cited by examiner

*Primary Examiner* — Phillip A Johnston
(74) *Attorney, Agent, or Firm* — Renner, Otto, Boisselle & Sklar, LLP

(57) ABSTRACT

An accessory device is provided that emits ultraviolet (UV) light and that receives electrical power from an electronic device (e.g., a smart phone). The accessory device notifies a user when the amount of UV light emitted by the accessory device is sufficient to sanitize a surface when the accessory device has been held at a predetermined distance from the surface.

20 Claims, 8 Drawing Sheets

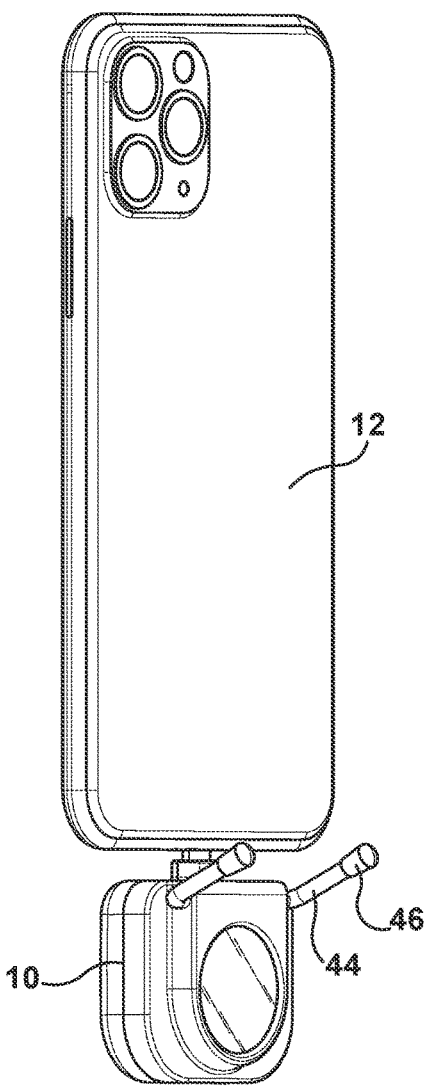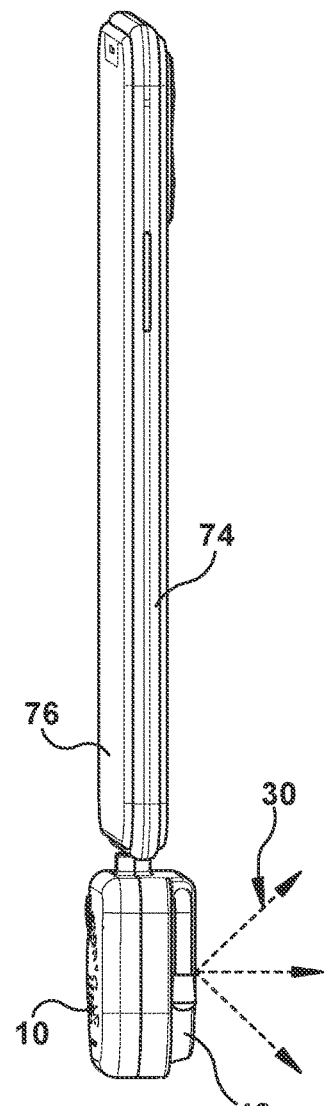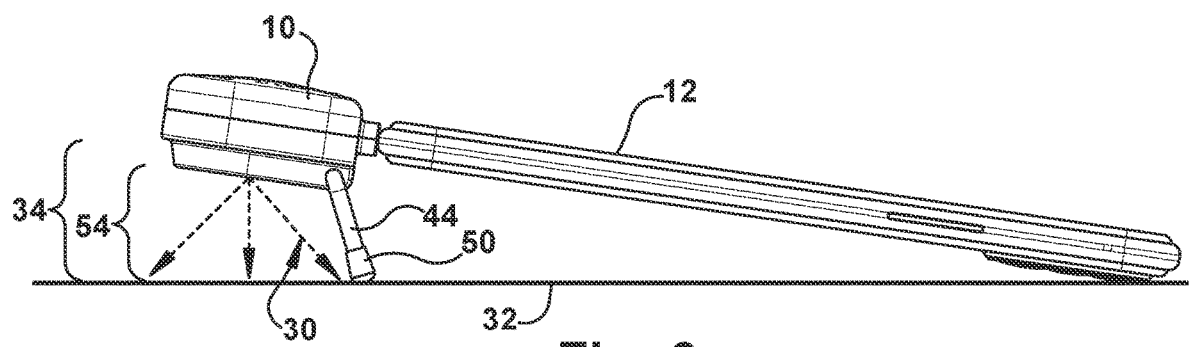

FIG. 18
10
FIG. 19
10
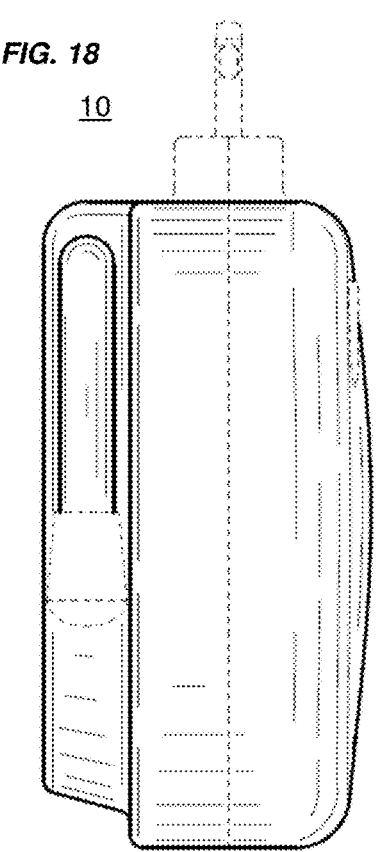
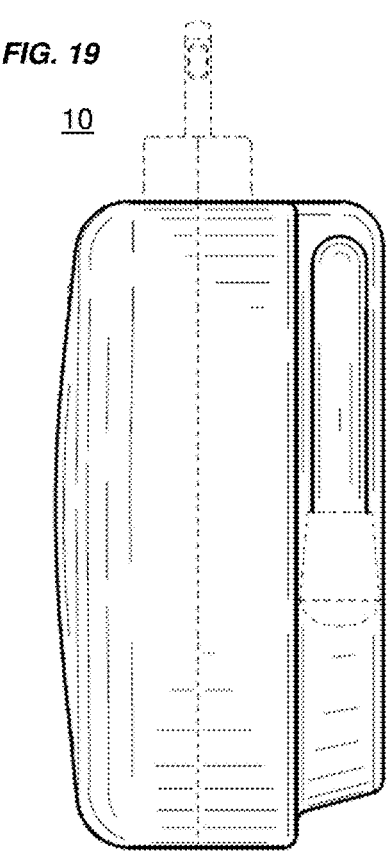
FIG. 20
10
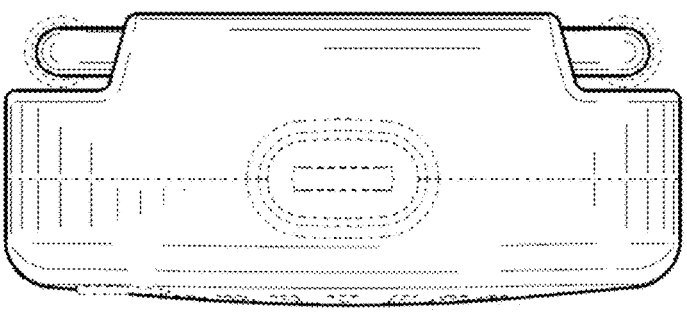
FIG. 21
10
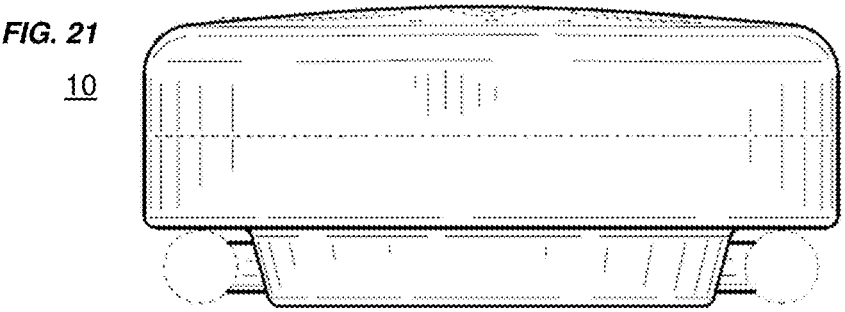

UVC SANITIZING ACCESSORY

TECHNICAL FIELD

The present disclosure relates generally to an accessory device for an electronic device and, more particularly, to a ultraviolet (UV) light emitting device receiving electrical power from a mobile device such as a smartphone.

BACKGROUND

Sanitizing of shared surface has become more widespread due to a greater understanding of the danger posed by germs. Frequently, surfaces are sanitized using chemicals (e.g., sprays and wipes) that may be difficult to carry and use outside of the home. Additionally, such chemicals are limited in supply and must be refilled as needed.

To avoid the difficulties posed by carrying and refilling such chemicals, people have begun to use devices emitting ultraviolet (UV) light to sanitize surfaces. However, it is difficult to ensure that surfaces are adequately being sanitized using such devices, because neutralizing germs on a surface is dependent on the optical power of the UV light incident on the surface.

SUMMARY

A sanitizing solution is needed that allows people to effectively sanitize surfaces and that is easily portable. The present disclosure provides an accessory device that emits ultraviolet (UV) light and that includes an indicator for notifying a user when a surface has been sanitized. The present disclosure also provides an accessory device (1) including a stand for maintaining a distance from a surface and (2) that emits UV light for an amount of time required for the UV light to neutralize a threshold percentage of germs on a surface at a predetermined distance from the light source based on the optical power of the light source.

According to one aspect of the disclosure, there is provided an accessory device for use with an electronic device. The accessory device includes a housing, a light source, a connector, a hardware input, and circuitry. The light source is positioned within the housing and configured to emit ultraviolet (UV) light. The connector receives electric power from the electronic device. The hardware input receives an instruction from a user. The circuitry receives the electric power from the connector and receives the instruction from the hardware input. When the light source is emitting UV light, the circuitry determines a time duration of light emission indicating a length of time that the light source has currently been emitting UV light. The circuitry controls the emission of the UV light by the light source, such that: when the light source is not currently emitting the UV light and the instruction is received, causing the light source to emit the UV light; when the light source is currently emitting the UV light and the time duration is less than a time threshold, the circuitry causes the light source to continue the emission of the UV light; and when the light source is currently emitting the UV light and the time duration is greater than the time threshold, the circuitry causes the light source to stop the emission of the UV light. The time threshold is an amount of time required for the UV light to neutralize a threshold percentage of germs on a surface at a predetermined distance from the light source based on the optical power of the light source.

Alternatively or additionally, further including an indicator for issuing a notification. The circuitry controls the issuing of the notification by the indicator based on the time duration of light emission.

Alternatively or additionally, the circuitry causes the notification issued by the indicator to vary depending on the time duration of light emission.

Alternatively or additionally, the indicator is configured to emit the notification as visible light.

Alternatively or additionally, the indicator includes multiple light emitters and the circuitry is configured to, based on the time duration of light emission, alter the notification by varying at least one of: a number of the multiple light emitters emitting the notification; a color of the notification; a brightness of the notification; or a flashing of the notification.

Alternatively or additionally, further including a sensor configured to measure an orientation of the accessory device and to output an orientation signal based on the measured orientation. The circuitry, at a first time point, receives the orientation signal from the sensor as an initial orientation. At subsequent time points following the first time point: the circuitry receives the orientation signal from the sensor as an updated orientation; determines whether the updated orientation varies from the initial orientation by more than an orientation threshold; and when the updated orientation varies from the initial orientation by more than the orientation threshold, the circuitry causes the light source to stop the emission of the UV light.

Alternatively or additionally, the sensor includes at least one of an accelerometer or a gyroscope.

Alternatively or additionally, further including a stand adjustably attached to the housing and configured to articulate between an extended position and a closed position. In the extended position, a distal end of the stand is located at a distance from the housing such that, when the stand is in the extended position and the distal end of the stand is placed against a surface, the surface is located at a distance of less than the predetermined distance from the light source. In the closed position, the distal end of the stand is located closer to the housing than in the extended position.

Alternatively or additionally, the light source emits UVC light in the 200 nm to 280 nm wavelength range.

Alternatively or additionally, the housing includes a visible opening formed by a quartz window positioned to allow the UVC light to exit the housing.

Alternatively or additionally, further including a reflector positioned within an interior volume of the housing and configured to reflect the UVC light towards the quartz window.

Alternatively or additionally, the light source includes UV light emitters configured to emit the UV light and a visible light emitter configured to emit visible light. The visible light emitter is configured to emit the visible light while the UV light emitters are emitting the UV light.

Alternatively or additionally, the circuitry is further configured to cause the light source to stop emitting UV light when the light source is currently emitting UV light and the instruction is received.

According to another embodiment, a method is provided for controlling an accessory device including a light source and circuitry, and receiving electrical power from an electronic device. The method includes receiving an instruction by the circuitry to begin light emission. The method causes the light source to emit ultraviolet (UV) light using the circuitry. The method determines a time duration of light emission indicating a length of time that the light source has currently been emitting UV light. When the time duration is less than a time threshold, the method causes the light source to continue the emission of the UV light. When the time duration is greater than the time threshold, the method causes the light source to stop the emission of the UV light using the circuitry. The time threshold is an amount of time required for the UV light to neutralize a threshold percentage of germs on a surface at a predetermined distance from the light source based on the optical power of the light source.

Alternatively or additionally, the accessory device further includes an indicator. The method further includes issuing a notification by the indicator based on the time duration of light emission, such that the notification varies depending on the time duration of light emission.

Alternatively or additionally, the indicator includes multiple light emitters. The method further includes, based on the time duration of light emission, altering the notification by varying at least one of: a number of the multiple light emitters emitting the notification; a color of the notification; a brightness of the notification; or a flashing of the notification.

Alternatively or additionally, the accessory device further includes a sensor configured to measure an orientation of the accessory device and to output an orientation signal based on the measured orientation. The method further includes, at a first time point, receiving with the circuitry the orientation signal from the sensor as an initial orientation. At subsequent time points following the first time point: the method receives with the circuitry the orientation signal from the sensor as an updated orientation; the method determines with the circuitry whether the updated orientation varies from the initial orientation by more than an orientation threshold; and, when the updated orientation varies from the initial orientation by more than the orientation threshold, the method causes the light source to stop emitting UV light using the circuitry.

Alternatively or additionally, the accessory device additionally includes a stand adjustably attached to the housing and configured to articulate between an extended position and a closed position. The method also extends the stand from the closed position to the extended position, such that a distal end of the stand is located at a distance from the housing. When the stand is in the extended position, the method places the distal end of the stand against a surface, such that the surface is located at a distance of less than the predetermined distance from the light source.

Alternatively or additionally, emitting the UV light comprises the light source emitting UVC light in the 200 nm to 280 nm wavelength range.

Alternatively or additionally, the light source includes UV light emitters configured to emit the UV light and a visible light emitter configured to emit the visible light. The method further includes, emitting the visible light while the UV light emitters are emitting the UV light.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

FIG. 5 is a back perspective view of the accessory device showing a stand in an extended position.

FIG. 6 is a side view of the accessory device showing a stand in the extended position and resting against a surface.

FIG. 7 is side view of the accessory device and electronic device of FIG. 5.

FIGS. 18 and 19 are side views of the accessory device.

FIG. 20 is a top view of the accessory device.

FIG. 21 is a bottom view of the accessory device.

Figure 1:
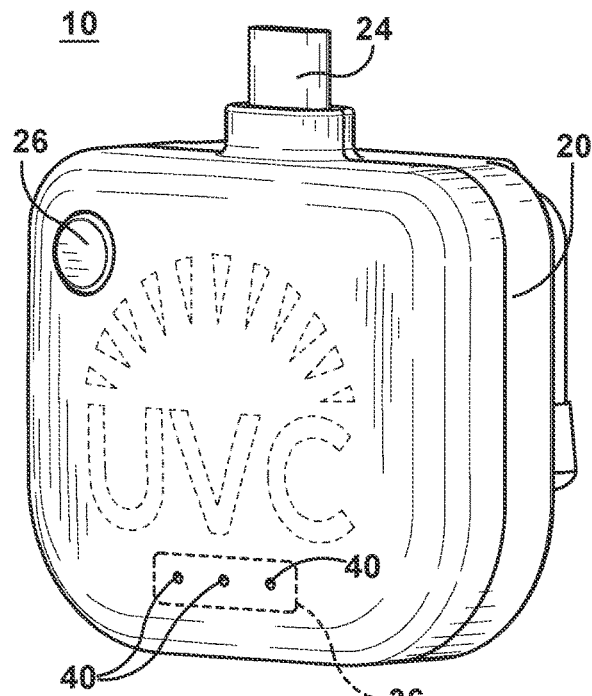
FIG. 1 is a front perspective view of a general embodiment of the accessory device.

The present invention is described below in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

DETAILED DESCRIPTION

According to a general embodiment, an accessory device is provided that emits ultraviolet (UV) light and that receives electrical power from an electronic device (e.g., a smart phone). The accessory device stops emitting the UV light when the amount of UV light emitted by the accessory device is sufficient to sanitize a surface located at a predetermined distance from the surface.

Turning to FIGS. 1-4, a general embodiment is shown of an accessory device 10 for use with an electronic device 12. The accessory device 10 includes a housing 20, a light source 22, a connector 24, a hardware input 26, and circuitry 28. The light source 22 is positioned within the housing 20 and emits UV light 30. The connector 24 receives electric power from the electronic device 12. The circuitry 28 receives the electric power from the connector 24. The circuitry 28 controls the emission of the UV light 30 by the light source 22. In a general embodiment, the circuitry 28 controls the light source 22 based on a time threshold. The time threshold is an amount of time required for the UV light 30 to neutralize a threshold percentage of germs on a surface 32 at a predetermined distance 34 from the light source 22 based on the optical power of the light emitted by the light source 22.

When the light source 22 is emitting UV light 30, the circuitry 28 determines a time duration of light emission. The time duration of light emission indicates a length of time that the light source 22 has currently been emitting UV light 30. When the light source 22 is currently emitting the UV light 30 and the time duration is less than a time threshold, the circuitry may cause the light source 22 to continue the emission of the UV light 30. Conversely, when the light source 22 is currently emitting the UV light 30 and the time duration is greater than the time threshold, the circuitry causes the light source 22 to stop the emission of the UV light 30.

In addition to controlling the light source 22 based on the time duration, the circuitry 28 may also issue notifications based on the time duration. For example, the accessory device may include an indicator 36 that issues a notification. The circuitry 28 may control the issuing of the notification by the indicator 36 based on the time duration of light emission. In one embodiment, the circuitry 28 causes the notification issued by the indicator 36 to vary depending on the time duration of light emission. For example, the indicator 36 may include multiple light emitters 40 and the notification may be emitted as visible light from the multiple light emitters 40. Based on the time duration of light emission, the circuitry 28 may alter the notification by varying at least one of: a number of the multiple light emitters emitting the notification, a color of the notification, a brightness of the notification, or a flashing of the notification.

Figure 2:
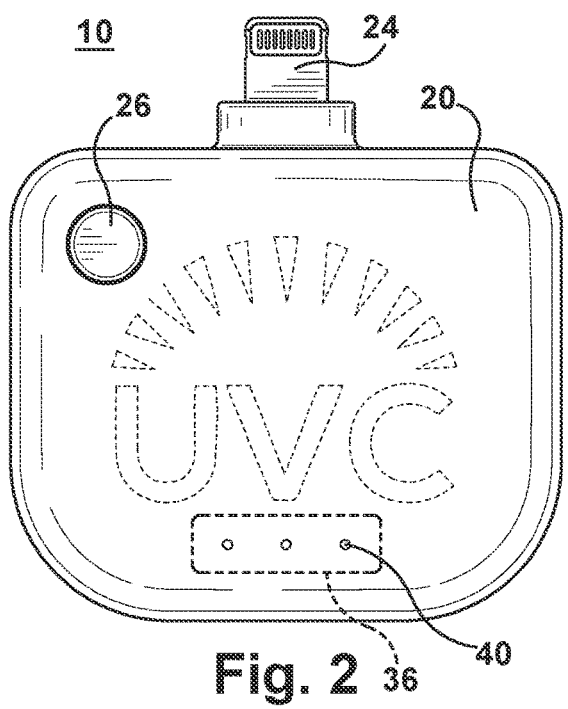
FIG. 2 is a front view of the accessory device of another embodiment of the accessory device.

As shown in FIGS. 1 and 2, the accessory device 10 includes a hardware input 26 for receiving an instruction from a user. The circuitry 28 receives the instruction from the hardware input 26. As shown, the hardware input 16 may be a physical button that a user presses to toggle light emission from the light source 22. That is, when the light source 22 is not currently emitting the UV light 30 and the instruction is received, the circuitry 28 causes the light source 22 to emit the UV light 30. Similarly, when the light source 22 is currently emitting UV light 30 and the instruction is received, the circuitry may cause the light source 22 to stop emitting UV light 30.

The hardware input 26 may be any suitable apparatus for receiving input from a user. For example, the hardware input 26 may be a mechanically actuated button, a capacitive button, a switch, etc.

In the embodiment shown in FIG. 2, the indicator 36 includes three light emitters 40. The light emitters 40 may be illuminated in sequence as the time duration progresses with time towards the time threshold. For example, a first light emitter 40 may flash when the time duration is less than one third of the time threshold. The first light emitter 40 may then emit light steadily when the time duration is greater than one third of the time threshold. A second light emitter 40 may flash when the time duration is greater than one third of the time threshold and less than two third of the time threshold. The second light emitter 40 may then emit light steadily when the time duration is greater than two thirds of the time threshold. A third light emitter 40 may flash when the time duration is greater than two thirds of the time threshold and less than the time threshold. The second light emitter 40 may then emit light steadily when the time duration is greater than the time threshold.

As described above, the time threshold is an amount of time required for the UV light 30 to neutralize a threshold percentage of germs on a surface 32 at a predetermined distance 34 from the light source 22 based on the optical power of the light source 22. The predetermined distance 34 may be 1.0 inches, 1.5 inches, 2 inches, or 2.5 inches. The threshold percentage may be 95%, 99%, or 99.9%. The time threshold may be 45 seconds, 60 seconds, or 90 seconds.

Figure 4:
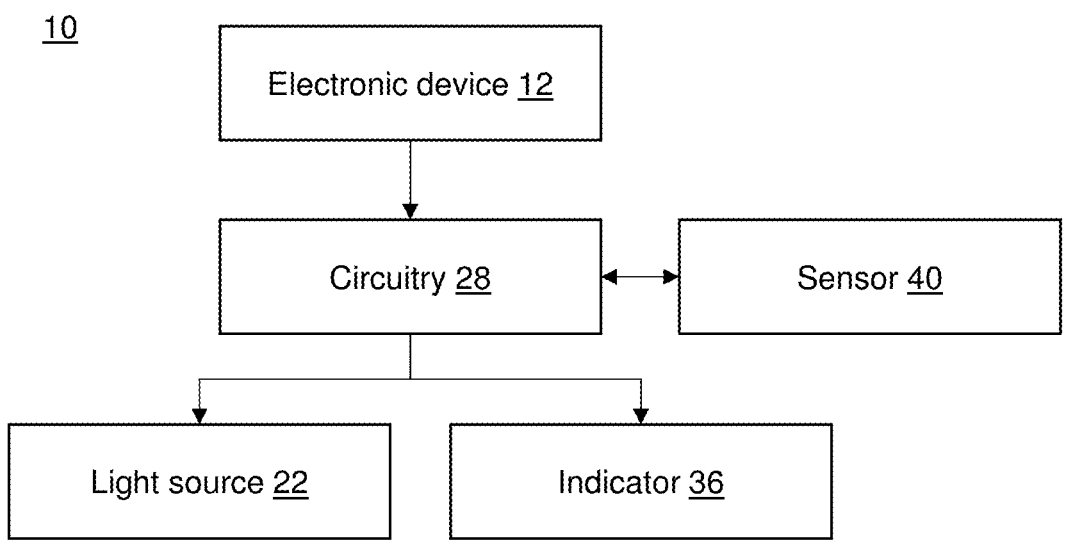
FIG. 4 is a schematic view of electrical components of the accessory device of FIG. 1.

In the embodiment shown in FIG. 4, the accessory device 10 additionally includes a sensor 40. The sensor 40 measures an orientation of the accessory device 10 and outputs an orientation signal based on the measured orientation. For example, the sensor 40 may be at least one of a gyroscope (e.g., three-axis gyroscope) or accelerometer (e.g., three-axis accelerometer). At a first time point, the circuitry 28 receives the orientation signal from the sensor 40 as an initial orientation. At subsequent time points following the first time point, the circuitry 28 receives the orientation signal from the sensor as an updated orientation.

The circuitry 28 determines whether the updated orientation varies from the initial orientation by more than an orientation threshold. For example, the orientation signal may include a value for the x, y, and z axis indicating movement or rotation of the accessory device 10 along the associated axis. The circuitry 28 may compare the initial orientation to each updated orientation as it is received. For example, upon the light source 22 beginning to emit the light 30 or just prior to the light source 22 beginning to emit the light 30, the initial orientation may be received from the sensor 40. At a certain update frequency (e.g., four times per second), the updated orientation signal may be received from the sensor 40. The initial orientation signal and the updated orientation signal may contain the same information and may only differ in the orientation reading measured by the sensor 40.

Upon receiving the updated orientation signal, the circuitry 28 may compare the updated orientation signal to the initial orientation signal using any suitable technique. For example, the circuitry 28 may calculate a distance (i.e., square root of the sum of the squared difference for the received data points) between the updated orientation signal and the initial orientation signal. When the updated orientation varies from the initial orientation by more than the orientation threshold, the circuitry 28 may cause the light source 22 to stop emitting the UV light 30. Otherwise, the light source 22 may continue to emit the UV light 30.

By stopping light emission when the accessory device 10 orientation changes user safety may be improved by reducing the risk that a user will be exposed to the UV light 30 when the accessory device 10 is dropped or fumbled by a user. That is, if a user stumbles while holding the accessory device 10 or drops the accessory device 10, the light source 22 may be shut off so that the user is not accidentally illuminated by the harmful UV light.

In the embodiment shown in FIGS. 5-7, the accessory device 10 may also include a stand 44. The stand 44 may be adjustably attached to the housing 20, such that the stand 44 is articulable between an extended position 46 and a closed position 48. For example, the stand 44 may be rotationally attached to the housing 20 so that the stand 44 is rotatable between the extended position 46 and the closed position 48. In the extended position shown in FIGS. 5 and 6, a distal end 50 of the stand is located at a distance from the housing 20 such that, when the stand 44 is in the extended position 46 and the distal end 50 of the stand 44 is placed against a surface 32, the surface 32 is located at a distance 54 of less than the predetermined distance 34 from the light source 22. In the closed position 48 shown in FIGS. 3 and 7, the distal end 50 of the stand 44 is located closer to the housing 20 than in the extended position 46.

Figure 9:
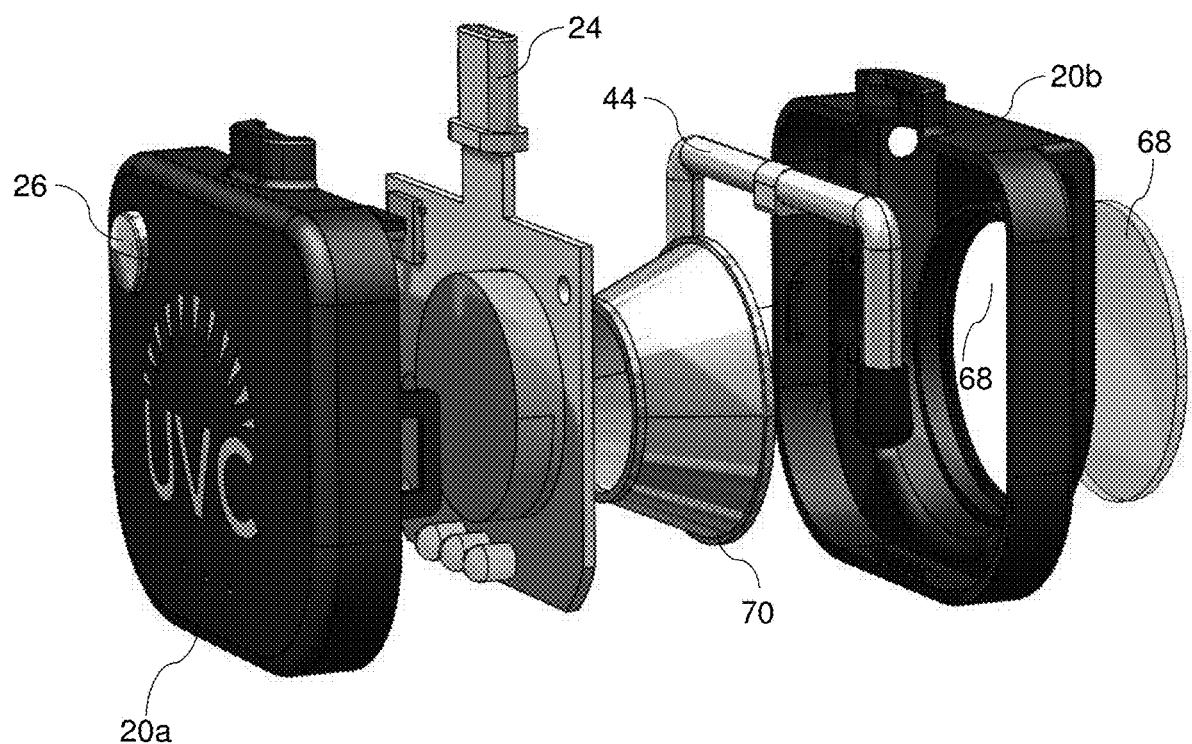
FIG. 9 is an exploded front view of the accessory device of FIG. 1.

In the embodiment shown in FIG. 6, the stand 44 is positioned in the extended state and the accessory device is attached to the electronic device 12. The combination of the accessory device 10 and the electronic device 12 may be rested against the surface 32 such that the stand 44 is used to maintain the surface 32 at the correct distance for a portion of the surface to be sanitized. That is, because proper sanitization depends on the optical power delivered to the surface 32 and because the optical power is effected by time of illumination and distance of the light source 22 from the surface 32 (e.g., due to the inverse square law), it is important that the surface 32 is not farther than the predetermined distance 34 from the light source 22. In FIG. 9, the accessory device 10 is sanitizing a horizontal surface 32, but the stand 44 may be similarly used to maintain a position of the light source 22 relative to a vertical surface or any other surface.

The stand 44 may be any suitable structure for maintaining a distance from a surface 32. In the depicted embodiments, the stand 44 is a U-shaped object including rubber tips at the distal ends 50. The stand 44 is not limited to this structure, but may have any suitable form. For example, the stand 44 could include a telescoping portion. Alternatively, the stand 44 could be a fixed structure that is not extendable between an extended position 46 and a closed position 48. In such an embodiment, the stand 44 may remain in the extended position 46. In still another embodiment, the stand 44 could form an enclosed shape (such as a square or triangle) with a corner or a side forming the distal end 50.

As described above, the light source 22 emits UV light. In one embodiment, the light source emits UVC light in the 200 nm to 280 nm wavelength range. UV light (also referred to as ultraviolet radiation) is most broadly defined as electromagnetic radiation in the range of 10-400 nm. However, short wave ultraviolet light (referred to as UVC) is the most effective for germicidal applications. UVC (also written as UV-C) includes wavelengths of 100-280 nm, although 240-280 nm are typically most effective for sanitizing or sterilizing airborne pathogens. In this wavelength range, UV light is most efficiently absorbed by DNA, with maximum absorption being at approximately 260 nm. The effectiveness of the UV radiation is directly related to intensity and exposure time.

The light source 22 may be any suitable source of UV light. In the embodiment shown in FIG. 4, the light source 22 includes multiple UV light emitters 60 that each emit the UV light. For example, each of the UV light emitters 60 may be UV emitting light emitting diodes (LEDs).

Figure 8:
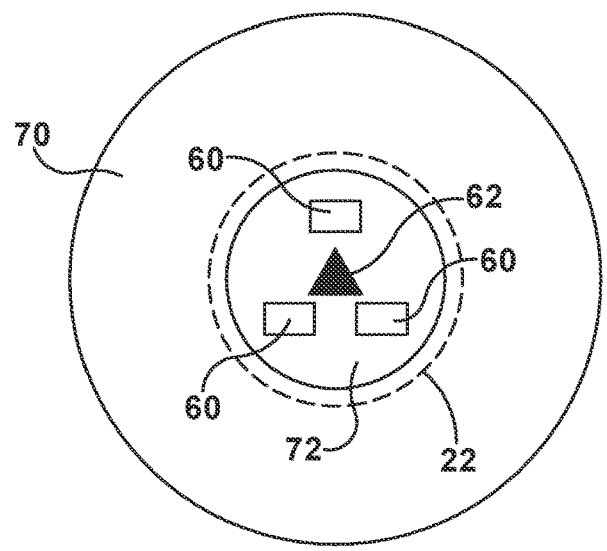
FIG. 8 is a schematic view of a light source and a reflector.

In the embodiment shown in FIG. 8, the light source 22 also includes a visible light emitter 62. The visible light emitter 62 emits visible light while the UV light emitters 60 are emitting the UV light 30. The visible light may be any suitable wavelength (e.g., purple or blue) and may be utilized for user-feedback purposes. That is, the visible light is used to notify a user when the invisible UV light is being emitted. In this way, by including a visible light emitter 62 in the light source 22, user safety may be improved by notifying a user when potentially harmful UV light is being emitted by the light source 22.

Figure 10:
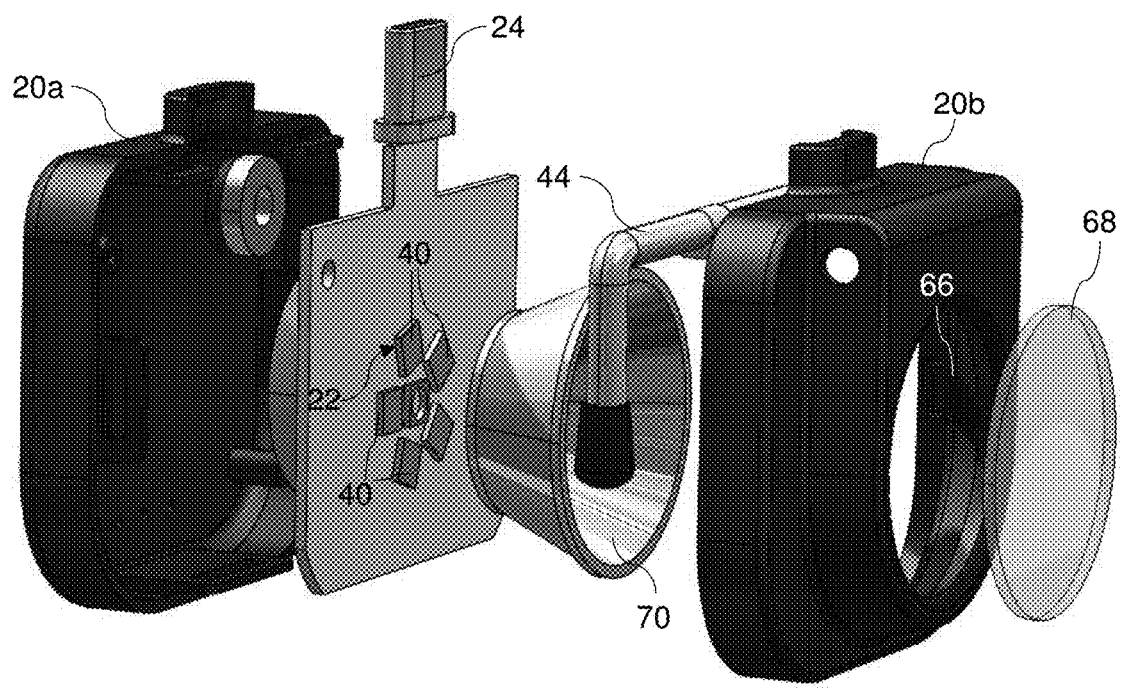
FIG. 10 is an exploded back view of the accessory device of FIG. 1.

As shown in FIGS. 9 and 10, the light source 22 may be maintained within an interior volume 64 of the housing 20. To allow the UV light 30 to exit the housing 20, the housing 20 may include a visible opening 66 formed by a quartz window 68 positioned to allow the UVC light 30 to exit the housing 20. For example, the visible opening 66 may be an opening or hole in the housing 20. To protect the light source 22 from damage, the visible opening 66 may include the quartz window 68 as a cover to protect against dust, liquids, and physical objects from entering through the visible opening 66 and damaging the light source 22. The quartz window 68 may be chosen (as opposed to plastic or different types of glass), because quartz is transparent to UVC light and allows for a greater percentage of UVC light generated by the light source 22 to exit from the housing 20.

The housing 20 may be made of any suitable material. For example, the housing 22 may be made or metal and/or plastic. As described above, the housing functions to protect the various components of the accessory device 10. For example, the light source 22, circuitry, and sensor 40 may all be housed within an interior volume of the housing 20.

The housing 20 may additionally include a reflector 70 positioned within the interior volume 64 of the housing 20. The reflector 70 may be positioned relative to the light source 22 such that the UV light 30 that interacts with the reflector 70 is reflected towards the quartz window 68. In this way, the reflector 70 may function to improve the optical power of the light source 22 by increasing the amount of light that successfully exits the housing 20.

The reflector 70 may be any structure reflective to the UV light 30. For example, the reflector may be a polished aluminum reflector cone. The inner surface of the reflector 70 may include a flat central portion 72 that the light source 22 is mounted to. In one example, the central portion 72 has cut outs aligned with the light emitters of the light source 22.

Figure 3:
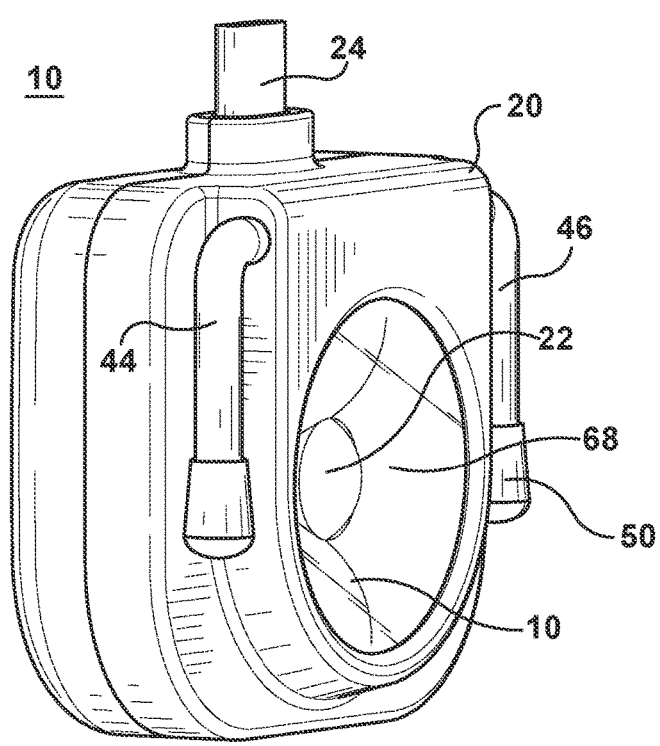
FIG. 3 is a back perspective view of the accessory device of FIG. 1.

As shown in FIGS. 1-3, the connector 24 may extend from the housing 20 to interact with the electronic device 12. In FIGS. 1 and 3, the connector 24 is a USB-C connector, while in FIG. 2 the connector is a Lightning connector. The connector 24 may establish an electrical connection with the electronic device 12 via any suitable standard.

Figures 11, 12:
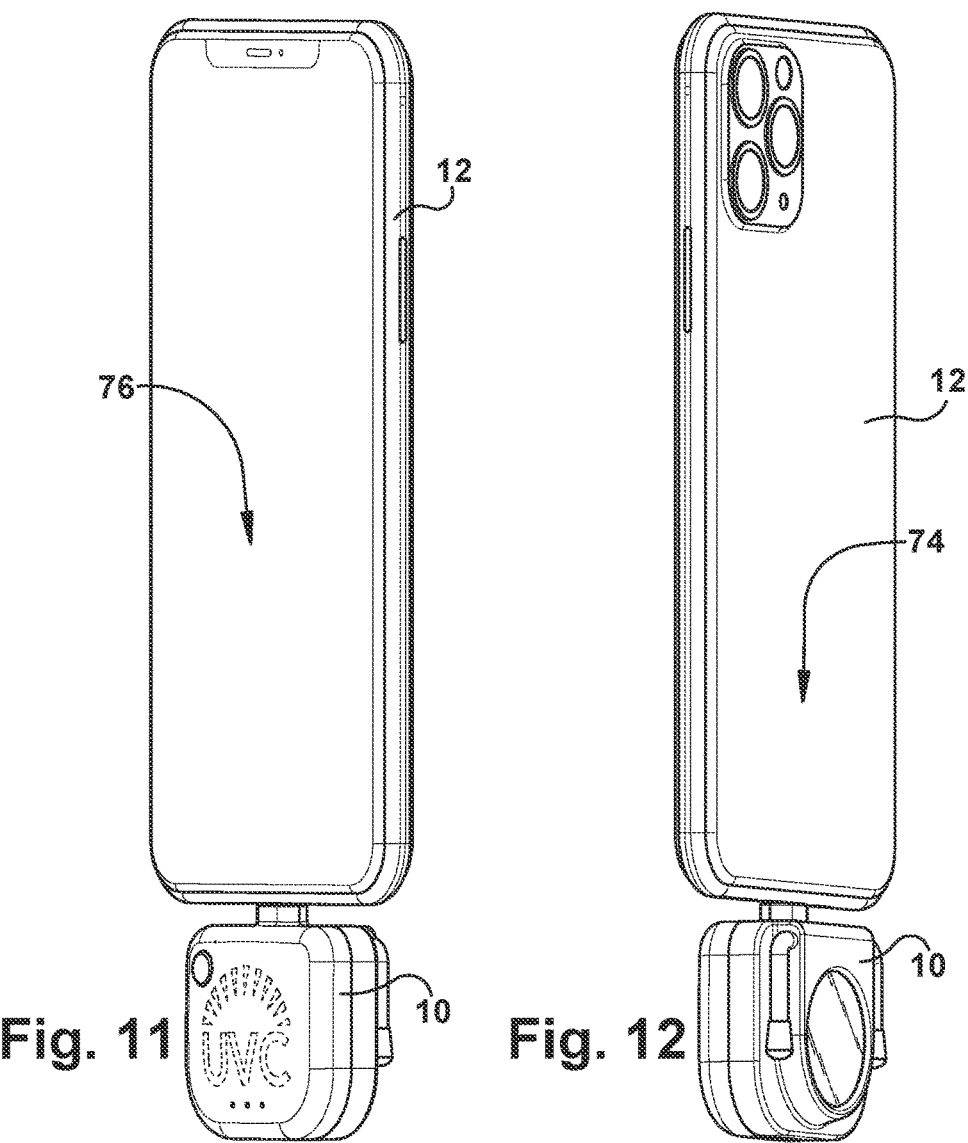
FIG. 11 is a front perspective view of the accessory device of FIG. 1 connected to an electronic device.
FIG. 12 is a back perspective view of the accessory device and electronic device of FIG. 5.

Turning to FIGS. 11 and 12, the electronic device 12 may be any suitable device capable of supplying electrical power to the accessory device 10 via the connector 24. For example, the electronic device 12 may be a smart phone or a table computer. The accessory device 10 may be connected to the electronic device 12 such that the UV light 30 is emitted towards a same direction facing a back surface 74 of the electronic device 12. In this way, a user may be prevented from shining UV light 30 towards their face when the user is facing a front surface 76 of the electronic device. Alternatively, the accessory device 10 may be connected to the electronic device 12 having any orientation supported by the connector 24.

The accessory device 10 may additionally include a battery that is changed via the electrical power received through the connector 24. The power supplied by the battery may be sufficient to perform one or more sterilization sessions (i.e., a sterilization session is emitting the UV light for a time duration at least equal to the time threshold).

Figure 13:
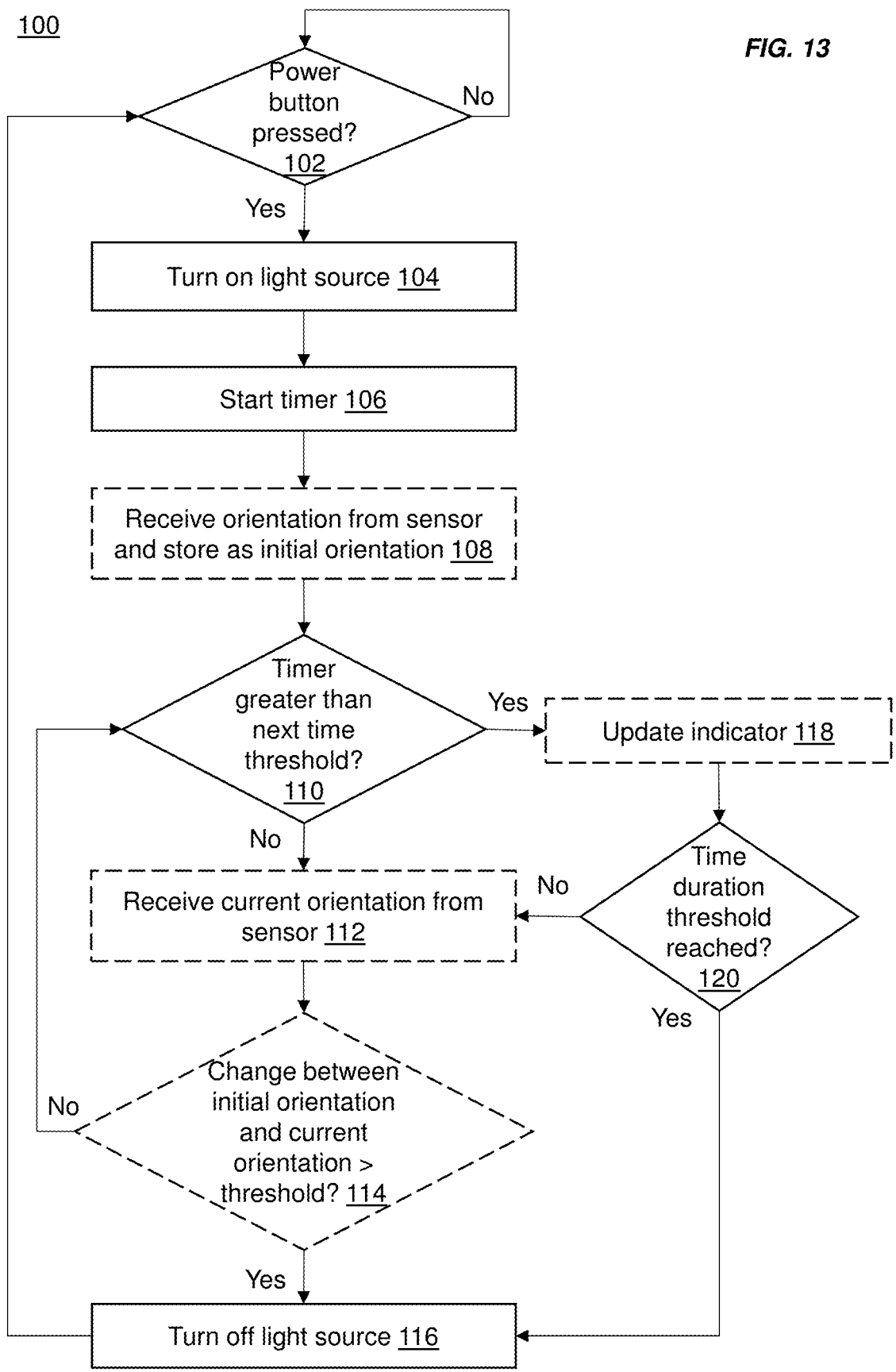
FIG. 13 is a flow diagram depicting a method of sanitizing a surface using the accessory device.
Figure 14:
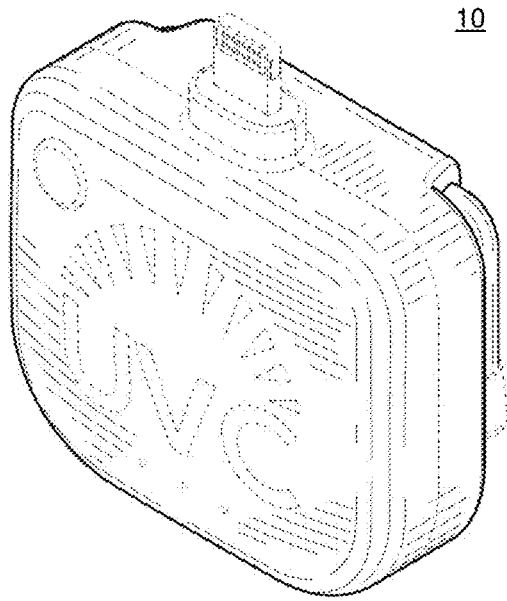
FIG. 14 is a front perspective view of the accessory device.
Figure 15:
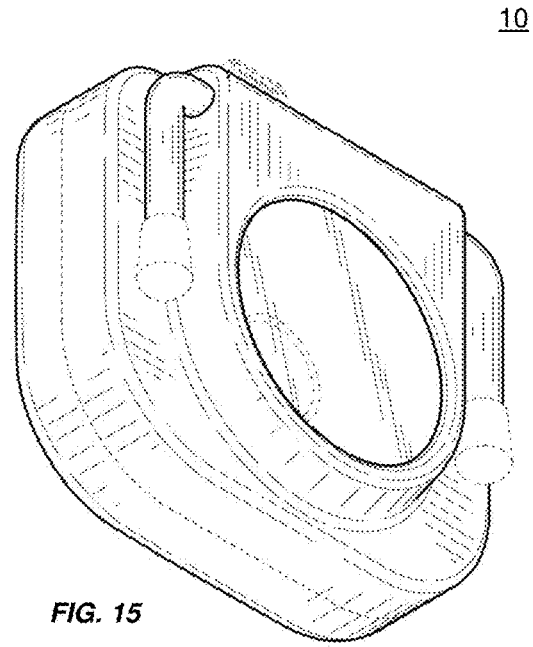
FIG. 15 is a back perspective view of the accessory device.
Figure 16:
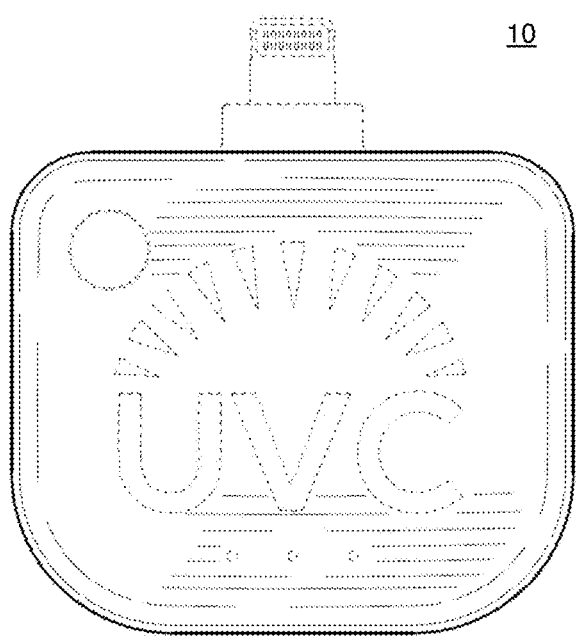
FIG. 16 is a front view of the accessory device.
Figure 17:
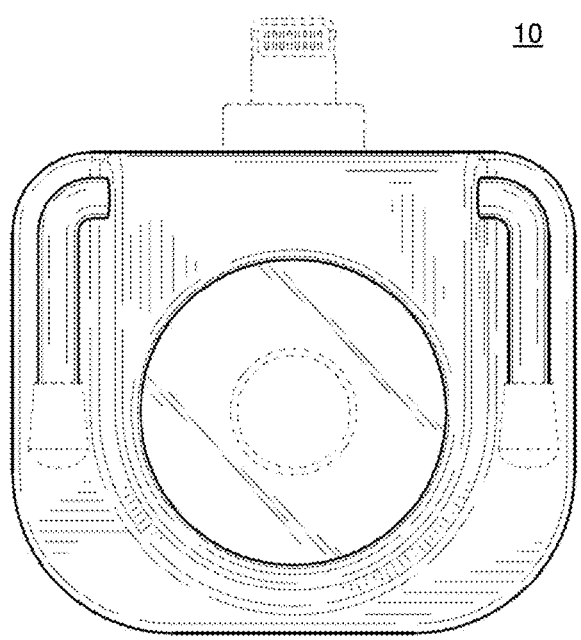
FIG. 17 is a back view of the accessory device.

Turning to FIG. 13, a method is shown for controlling the accessory device 10. In decision block 102, a check is performed to see if an instruction has been received by the interface 26. When an instruction is received by the interface 26 to begin light emission, then processing proceeds to process block 104. In process block 104, the circuitry causes the light source 22 to emit the UV light 30.

In process block 106, the circuitry determines a time duration of light emission indicating a length of time that the light source has currently been emitting UV light. As shown in the figure, this may include starting a timer 106 when light emission begins. In decision block 110, a check is performed to determine if the next time threshold has been reached. For example, the method 100 may include a time duration threshold (signifying when the light source 22 should be turned off) and one or more indicator thresholds (signifying when the indicator 36 should be updated). In the example described above, the indicator 36 includes three light emitters. The method 100 may include one or more time thresholds associated with each of the three light emitters signifying when each of the light emitters should be turned on, flash, change color, etc.

In decision block 120, a check is performed to determine if the time duration is less than a time duration threshold. When the time duration is greater than the time threshold, then processing moves to process block 116 and the circuitry 28 causes the light source 22 to stop the emission of the UV light 30. Conversely, when the time duration is less than the time threshold, the light source 28 continues the emission of the UV light 30 and processing returns to decision block 110.

The method 100 may also be used to update the indicator 36 based on the time duration. For example, in optional process block 118, the indicator 36 may be updated when a next time threshold 110 is passed.

As described above, the accessory device 10 may include a sensor 40 for measuring orientation. In optional process block 108, the circuitry 28 receives the orientation signal from the sensor 40 as an initial orientation. If the timer is not greater than the text time threshold (110) or the time duration threshold has not been reached (120) then processing continues to optional process block 112. In optional process block 112, the circuitry 28 receives the orientation signal from the sensor 40 as an updated orientation. In decision block 114, the circuitry 28 determines whether the updated orientation varies from the initial orientation by more than an orientation threshold. When the updated orientation varies from the initial orientation by more than the orientation threshold, processing continues to process block 116 and the circuitry 28 causes the light source 22 to stop emitting UV light 30. If not, then processing returns to decision block 110.

FIGS. 14-21 depict different views of the accessory device 10. The broken lines shown in the figures may be for illustrative purposes only and may not form part of a claimed design.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. An accessory device for use with an electronic device, the accessory device comprising:
    a housing;
    a light source positioned within the housing and configured to emit ultraviolet (UV) light;
    a connector configured to receive electric power from the electronic device when connected to the electronic device;
    a hardware input configured to receive an instruction from a user; and
    circuitry configured to:
        receive the electric power from the connector;
        receive the instruction from the hardware input;
        when the light source is emitting UV light, determine a time duration of light emission indicating a length of time that the light source has currently been emitting UV light; and
        control the emission of the UV light by the light source, such that:
            when the light source is not currently emitting the UV light and the instruction is received, causing the light source to emit the UV light;
            when the light source is currently emitting the UV light and the time duration is less than a time threshold, causing the light source to continue the emission of the UV light; and
            when the light source is currently emitting the UV light and the time duration is greater than the time threshold, causing the light source to stop the emission of the UV light;
        wherein the time threshold is an amount of time required for the UV light to neutralize a threshold percentage of germs on a surface at a predetermined distance from the light source based on the optical power of the light source.

2. The accessory device of claim 1, further comprising an indicator configured to issue a notification, wherein the circuitry is further configured to control the issuing of the notification by the indicator based on the time duration of light emission.

3. The accessory device of claim 2, wherein the circuitry causes the notification issued by the indicator to vary depending on the time duration of light emission.

4. The accessory device of claim 3, wherein the indicator is configured to emit the notification as visible light.

5. The accessory device of claim 4, wherein the indicator includes multiple light emitters and the circuitry is configured to, based on the time duration of light emission, alter the notification by varying at least one of:
    a number of the multiple light emitters emitting the notification;
    a color of the notification;
    a brightness of the notification; or
    a flashing of the notification.

6. The accessory device of claim 1, further comprising a sensor configured to measure an orientation of the accessory device and to output an orientation signal based on the measured orientation, wherein:
the circuitry is further configured to:
at a first time point, receive the orientation signal from the sensor as an initial orientation; and
at subsequent time points following the first time point:
receive the orientation signal from the sensor as an updated orientation;
determine whether the updated orientation varies from the initial orientation by more than an orientation threshold; and
when the updated orientation varies from the initial orientation by more than the orientation threshold, cause the light source to stop the emission of the UV light.

7. The accessory device of claim 6, wherein the sensor includes at least one of an accelerometer or a gyroscope.

8. The accessory device of claim 1, further comprising a stand adjustably attached to the housing and configured to articulate between an extended position and a closed position, wherein:
in the extended position, a distal end of the stand is located at a distance from the housing such that, when the stand is in the extended position and the distal end of the stand is placed against a surface, the surface is located at a distance of less than the predetermined distance from the light source; and
in the closed position, the distal end of the stand is located closer to the housing than in the extended position.

9. The accessory device of claim 1, wherein the light source emits UVC light in the 200 nm to 280 nm wavelength range.

10. The accessory device of claim 1, wherein the housing includes a visible opening formed by a quartz window positioned to allow the UVC light to exit the housing.

11. The accessory device of claim 1, further comprising a reflector positioned within an interior volume of the housing and configured to reflect the UVC light towards the quartz window.

12. The accessory device of claim 1, wherein:
the light source includes UV light emitters configured to emit the UV light and a visible light emitter configured to emit visible light; and
the visible light emitter is configured to emit the visible light while the UV light emitters are emitting the UV light.

13. The accessory device of claim 1, wherein the circuitry is further configured to cause the light source to stop emitting UV light when the light source is currently emitting UV light and the instruction is received.

14. A method of controlling an accessory device including a light source and circuitry, and receiving electrical power from an electronic device when the accessory device is connected to the electronic device, the method including:
receiving an instruction by the circuitry to begin light emission;
causing the light source to emit ultraviolet (UV) light using the circuitry;
determine a time duration of light emission indicating a length of time that the light source has currently been emitting UV light; and
when the time duration is less than a time threshold, causing the light source to continue the emission of the UV light; and
when the time duration is greater than the time threshold, causing the light source to stop the emission of the UV light using the circuitry;
wherein the time threshold is an amount of time required for the UV light to neutralize a threshold percentage of germs on a surface at a predetermined distance from the light source based on the optical power of the light source.

15. The method of claim 14, wherein:
the accessory device further includes an indicator; and
the method further comprises issuing a notification by the indicator based on the time duration of light emission, such that the notification varies depending on the time duration of light emission.

16. The method of claim 15, wherein:
the indicator includes multiple light emitters; and
the method further comprises, based on the time duration of light emission, altering the notification by varying at least one of:
a number of the multiple light emitters memitting the notification;
a color of the notification;
a brightness of the notification; or
a flashing of the notification.

17. The method of claim 14, wherein:
the accessory device further includes a sensor configured to measure an orientation of the accessory device and to output an orientation signal based on the measured orientation;
the method further comprises:
at a first time point, receiving with the circuitry the orientation signal from the sensor as an initial orientation; and
at subsequent time points following the first time point:
receiving with the circuitry the orientation signal from the sensor as an updated orientation;
determining with the circuitry whether the updated orientation varies from the initial orientation by more than an orientation threshold; and
when the updated orientation varies from the initial orientation by more than the orientation threshold, causing the light source to stop emitting UV light using the circuitry.

18. The method of claim 14, wherein:
the accessory device additionally includes a stand adjustably attached to the housing and configured to articulate between an extended position and a closed position; and
the method further comprises:
extending the stand from the closed position to the extended position, such that a distal end of the stand is located at a distance from the housing; and
when the stand is in the extended position, placing the distal end of the stand against a surface, such that the surface is located at a distance of less than the predetermined distance from the light source.

19. The method of claim 14, wherein emitting the UV light comprises the light source emitting UVC light in the 200 nm to 280 nm wavelength range.

20. The method of claim 14, wherein:
the light source includes UV light emitters configured to emit the UV light and a visible light emitter configured to emit the visible light; and
the method further includes, emitting the visible light while the UV light emitters are emitting the UV light.

* * * * *